United States Patent [19]

Liang et al.

[11] Patent Number: 5,081,397
[45] Date of Patent: Jan. 14, 1992

[54] ATMOSPHERIC PRESSURE CAPACITIVELY COUPLED PLASMA ATOMIZER FOR ATOMIC ABSORPTION AND SOURCE FOR ATOMIC EMISSION SPECTROSCOPY

[75] Inventors: Dong C. Liang, Vancouver; Michael W. Blades, Surrey, both of Canada

[73] Assignee: University of British Columbia, Vancouver, Canada

[21] Appl. No.: 378,263

[22] Filed: Jul. 11, 1989

[51] Int. Cl.$^5$ ............................................. H01J 49/04
[52] U.S. Cl. ........................ 315/111.21; 313/231.38; 356/311; 356/316; 250/425
[58] Field of Search ............. 315/111.21; 313/231.31; 356/311, 316; 250/425

[56] References Cited

U.S. PATENT DOCUMENTS

| | | | |
|---|---|---|---|
| 3,569,777 | 3/1971 | Beaudry | 315/111.21 |
| 4,473,736 | 9/1984 | Bloyet et al. | 313/231.31 X |
| 4,479,075 | 10/1984 | Elliott | 315/111.21 |
| 4,556,318 | 12/1985 | Barnes et al. | |
| 4,810,933 | 3/1989 | Moisan et al. | 315/111.21 X |
| 4,950,956 | 8/1990 | Asamaki et al. | 315/111.21 |

OTHER PUBLICATIONS

R. H. Wendt & V. A. Fassel, "Atomic Absorption Spectroscopy with Induction-Coupled Plasma", Anal. Chem., 1966, 38, 337.
Greenfield et al., "Atomic Absorption with an Electrodeless High-Frequency Plasma Torch", Anal. Chim. Acta, 1968, 41, 385.
C. Veillon & M. Margoshes, "An Evaluation of the Induction-Coupled, Radio-Frequency Plasma Torch for Atomic Emission and Atomic Absorption Spectrometry", Spectrochim. Acta, 1968, 23B, 503.
B. Magyar & F. Aeschbach, "Why Not ICP as Atom Reservoir for AAS?", Spectrochim. Acta, 1980, 35B, 839.
D. C. Liang & M. W. Blades, "Atmospheric Pressure Capacitively Coupled Plasma Atomizer for Atomic Absorption Spectrometry", Anal. Chem. 1988, 60, 27.

The Pittsburgh Conference & Exposition, Paper No. 415 and 1140 (1988).
Improved Hollow Cathode Lamps for Atomic Spectroscopy 1985, Ed. S. Caroli, Ellis Horwood Limited.
J. A. C. Broekaert, "State of the Art of Glow Discharge Lamp Spectrometry Plenary Lecture", J. Anal. At. Spectrom. 1987, 2, 537.
P. Hannaford and A. Walsh, "Sputtered Atoms in Absorption and Fluorescence Spectroscopy", Spectrochem. Acta. 43B (1988), 1053.
A. E. Bernhard, "Atomic Absorption Spectrometry Using Sputtering Atomization of Solid Samples", Spectroscopy, 2, No. 6, 24 (1987).
Transactions of the Conference and School on the Elements, Techniques and Applications of Sputtering, 1 (1969).
R. Stephens, "Observation of Sputtering at Atmospheric Pressure", J. Anal. At. Spectrom. 3, 1137 (1988).

(List continued on next page.)

Primary Examiner—Eugene R. LaRoche
Assistant Examiner—Do Hyun Yoo
Attorney, Agent, or Firm—Christie, Parker & Hale

[57] ABSTRACT

A novel atmospheric pressure capacitively coupled ratio frequency plasma discharge method and apparatus. The apparatus is suitable for atomic absorption and atomic emission analysis of discrete sample volumes (1–50 $\mu$l). The plasma can be operated at very low Radio Frequency (RF) input powers (10–600 W) which allow for optimal conditions for atom resonance line absorption measurements. Sample vaporization for analysis in the plasma is done by an electrically heated tantalum strip vaporizer. The vaporization and dissociation-atomization steps are separately controlled. Analyte absorption takes place in the plasma discharge which is characterized by a long path length (10–50 cm) and low support gas flow rate (0.05 to 6 L/m) both of which provide for a relatively long residence time. The device exhibits linear calibration plots and provides sensitivities in the range of from 3.5–40 pg.

28 Claims, 7 Drawing Sheets

OTHER PUBLICATIONS

A. Montaser & V. A. Fassel, Anal. Chem. 1976, 48, 1490.
D. R. Demers, Spectrochim. Acta, 1985, 40B, 105.
R. S. Houk, V. A. Fassel, G. D. Flesch, H. J. Svec, A. L. Gray & C. E. Talor, Anal. Chem., 1980, 52, 2283.
A. L. Gray, Spectrochim. Acta, 1985, 40B, 1525.
G. Gillson & G. Horlick, Spectrochim. Acta 41B, 431 (1986).
P. Hannaford & A. Walsh, Spectrochim. Acta 43B, 1053 (1988).
H. J. Kim & E. H. Piepmeier, Anal. Chem. 60, 2040 (1988).
G. K. Wehner, Advances in Electronics and Electron Phys., 7, 239 (1955).

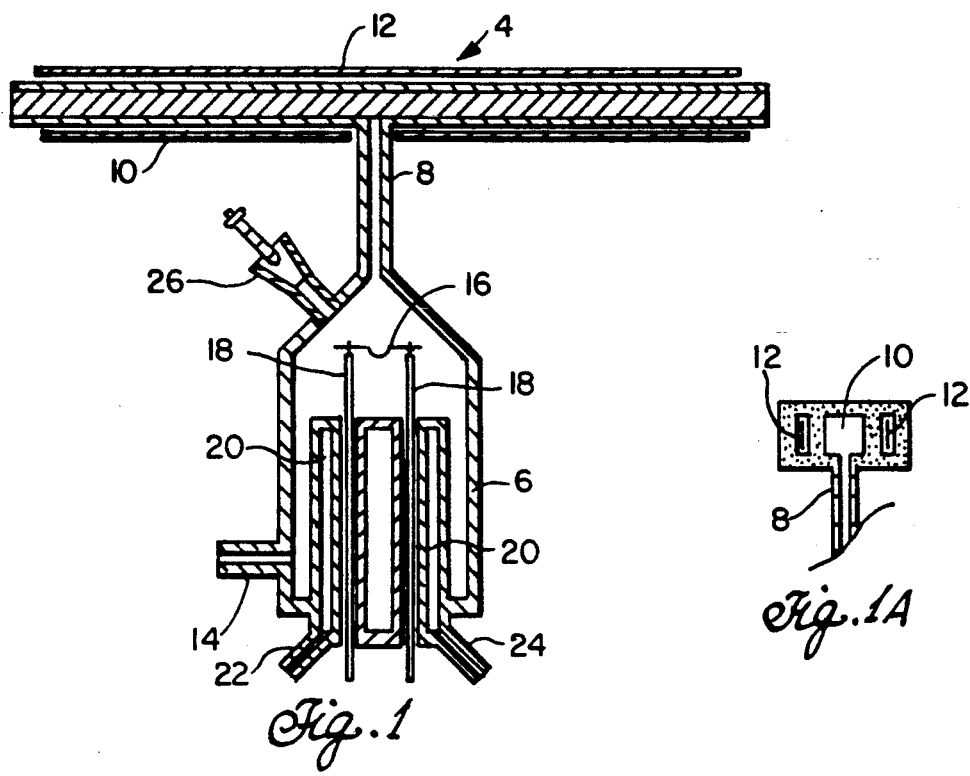
Fig. 1
Fig. 1A
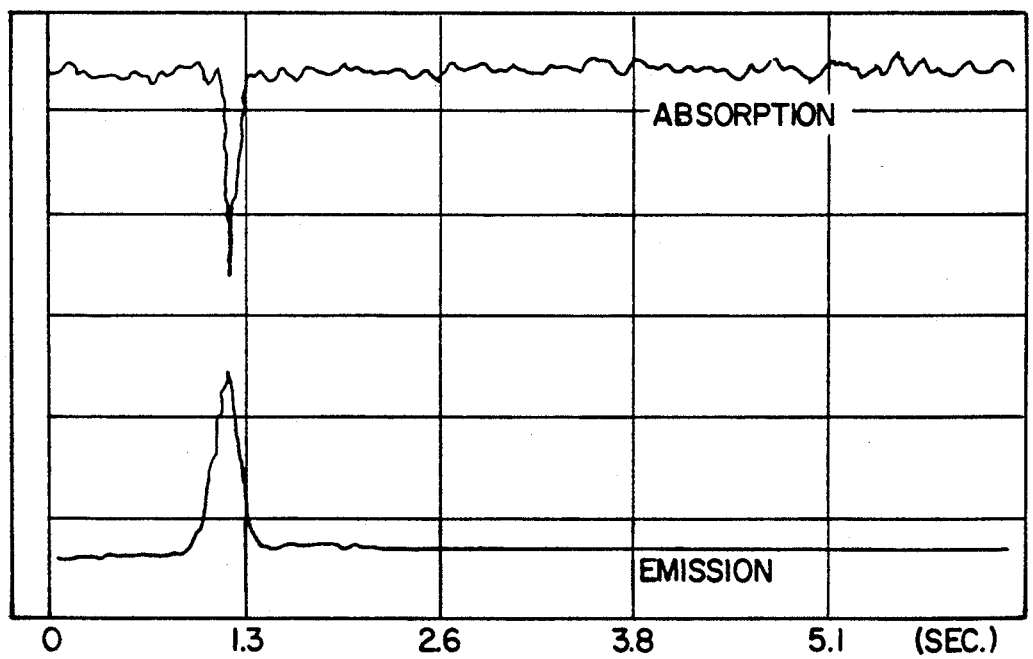
ABSORPTION AND EMISSION SIGNALS FOR 100 ng BORON AT 249.8 nm
Fig. 3

BACKGROUND EMISSION OF Ar PLASMA

BACKGROUND EMISSION OF He PLASMA

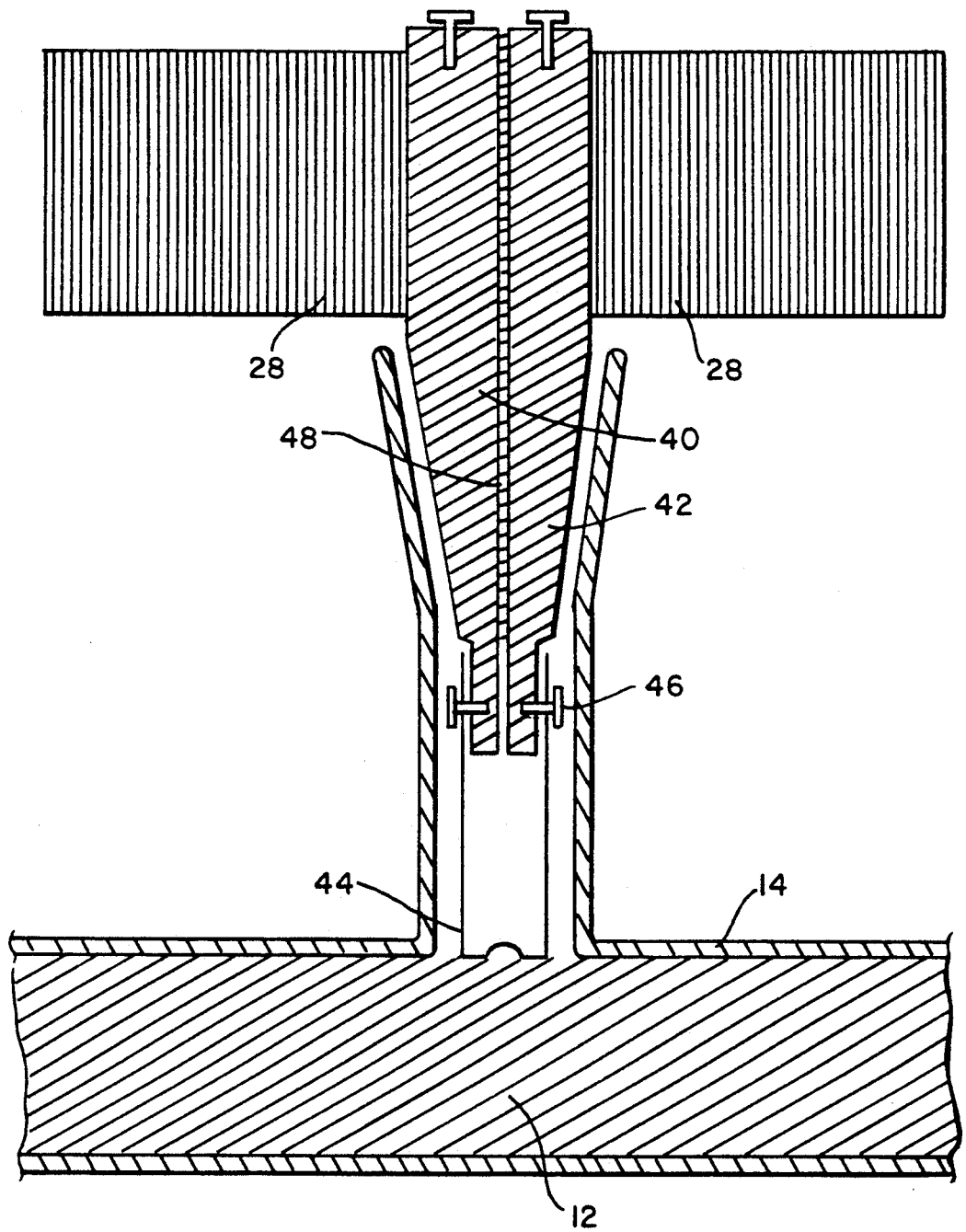

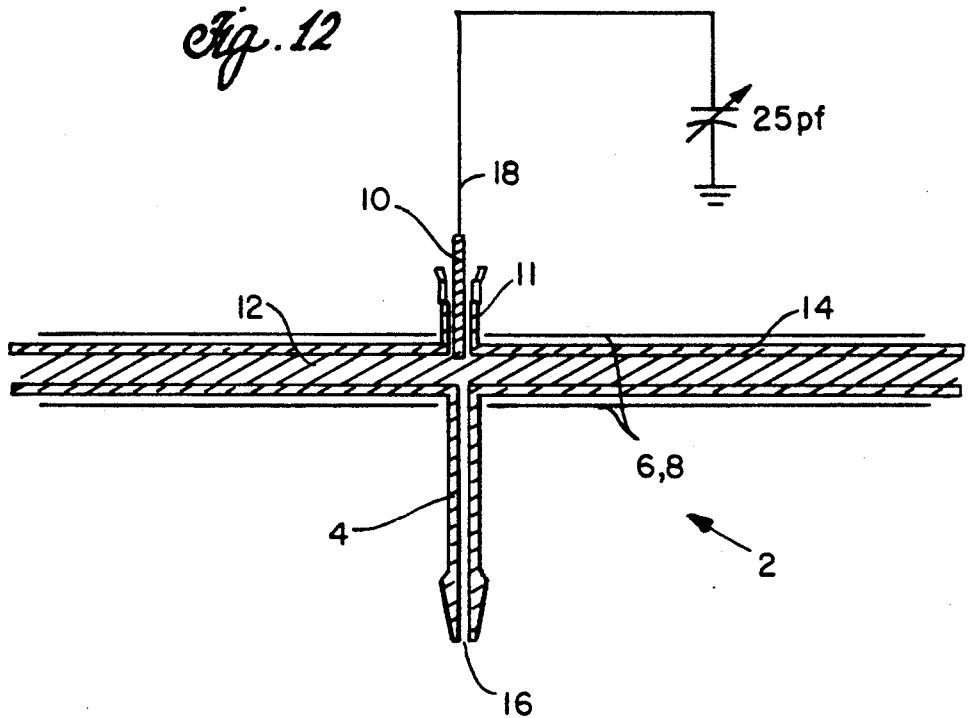
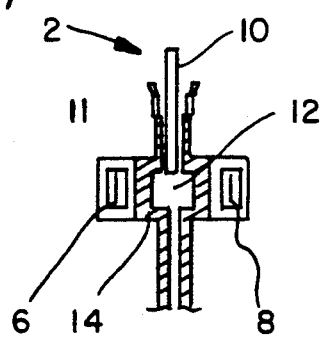

ATMOSPHERIC PRESSURE CAPACITIVELY COUPLED PLASMA ATOMIZER FOR ATOMIC ABSORPTION AND SOURCE FOR ATOMIC EMISSION SPECTROSCOPY

FIELD OF THE INVENTION

This application relates to a novel method and apparatus for the generation of an atmospheric pressure plasma and for conducting atomic absorption and emission analysis.

BACKGROUND OF THE INVENTION

During the past two decades inductively coupled plasma optical emission spectroscopy (ICP-OES) has played an important role in elemental analysis ICP-OES possesses several distinct advantages over other atomic methods including simultaneous multi-element capability, relative freedom from chemical interferences, low detection limits, and a large linear dynamic range. In recent years the ICP has also been used as a source for multi-element atomic fluorescence spectrometry (AFS) (see A. Montaser and V.A. Fassel, Anal. Chem., 1976, 48, 1490 and D.R. Demers, Spectrochim. Acta, 1985, 40B, 105) and plasma source mass spectrometry (ICP-MS) (see R.S. Houk, V.A. Fassel, G.D. Flesch, H.J. Svec, A.L. Gray, and C.E. Talor, Anal. Chem., 1980, 52, 2283 and A.L. Gray, Spectrochim. Acta, 1985, 40B, 1525). However, to date, the ICP has not been successfully exploited as an atomizer for atomic absorption spectrometry (AAS).

The properties of the ICP as an atom reservoir for AAS have been investigated by Wendt and Fassel (R.H. Wendt and V.A. Fassel, Anal. Chem., 1966, 38, 337), Greenfield et. al. (S. Greenfield, P.B. Smith, A.E. Breeze, and N.M.D. Chilton, Anal. Chim. Acta, 1968, 41, 385), and Veillon and Margoshes (C Veillon and M. Margoshes, Spectrochim. Acta, 1968, 23B, 503). In addition, Magyar and Aeschbach [B. Magyar and F. Aeschbach, Spectrochim. Acta, 1980, 35B, 839) have studied the theoretical implications of using the ICP for AAS. They concluded that the ICP provided sensitivities a factor of ten poorer than those exhibited by a flame. The relatively low sensitivity of ICP-AAS can be attributed to several factors. A relatively high support gas flow rate is required to operate an ICP and this acts to dilute the sample atoms. The absorption volume in an ICP is not optimum for AAS, in particular, the absorption path length is relatively short and this combined with the high aerosol transport rate means that the residence time of analyte atoms in the absorption volume is short. Moreover, traditional AAS primarily makes use of atomic resonance lines but in the ICP the high temperature favours the production of ionic species.

In spite of these factors, a plasma environment does offer several distinctive features which suggest that it could offer several advantages over flames and graphite furnaces for atomic absorption measurements. The relatively high temperature promotes complete vaporization and dissociation and thus aids in the control of chemical interferences. In addition, radio frequency (RF) plasmas are relatively stable and easy to control. The atom reservoir temperature, and hence the characteristics of the absorption volume, can be controlled by controlling the input power to the plasma. Also, since a plasma can be made to operate with a variety of gases (e.g. Ar, He, $N_2$. $H_2$, etc.) the gas phase chemistry can be controlled separately from mechanisms causing energy production. Finally, the shape and extent of a plasma can be controlled through appropriate design of the external electrodes used to couple the RF power into the plasma.

U.S. Pat. No. 4,556,318, Barnes et al., discloses a spectroanalytical system which includes induction coupled plasma apparatus for exciting sample material to an atomic state for analysis.

The inventors have published in Spectrodumica Acta, 1988, a paper entitled An Atmospheric Pressure Capacitively Coupled Plasma Atomizer For Atomic Absorption And Emission Spectroscopy outlining a prior two compartment design of atmospheric pressure capacitively coupled plasma atomizer.

The development and characterization of an atmospheric pressure, capacitively coupled plasma (CCP) torch for atomic absorption spectrometry (AAS) has been specifically described D. C. Liang and M.W. Blades, Anal. Chem. 60, 27 (1988)]. Subsequent work has demonstrated that this device can also be used quite effectively as a source for atomic emission spectrometry (AES) [D.C. Liang and M.W. Blades, Abstracts, The Pittsburgh Conference & Exposition, paper No. 415 and 1140 (1988)]. The configuration described previously was designed for the analysis of small volumes of liquid samples of a size typically analyzed by electrothermal atomization AAS (5-50 $\mu$L). However, the CCP can also be combined with other sample introduction techniques including laser ablation. The CCP developed for AAS was characterized by a long path length (20 cm) small diameter plasma sustained by capacitive coupling. The plasma could be operated at support-gas flow rates as low as 0.2 L/m and at radio frequency (rf) input powers between 30 to 600 W. Both the long path length tube geometry of the discharge and low support-gas flow rates acted to maximize analyte residence time in the plasma resulting in detection limits in the ng/L range.

By far the most important commercial spectral lamp for AAS and AFS is the hollow cathode lamp (HCL). The main advantages of the HCL are its very small spectral line-width and its high signal to background ratio. However, the absolute intensity of emission from the HCL is relatively low compared with the radiation from other plasma sources. To overcome this problem techniques such as direct current (dc) boosted-HCL, rf boosted-HCL, microwave coupled HCL, and high current pulsed HCL have been developed [Improved Hollow Cathode Lamps for Atomic Spectroscopy 1985, Ed. S. Caroli, Ellis Horwood Limited]. Additionally, the intensities of ion lines in HCLs are very weak, due to the dominant population of ground state atom in glow discharges [J.A.C. Broekaert, J. Anal. At. Spectrom. 2, 537 (1987)]. The factors contributing to the relatively low sensitivities of inductively coupled plasma (ICP)-AAS have been discussed previously by the inventors in the cited papers. One of the factors is that traditional AAS primarily makes use of atomic resonance lines; however there is a large population of ground state analyte ions in ICP's even at relatively low powers [G. Gillson and G. Horlick, Spectrochim. Acta 41B, 431 (1986)]. The development of an intense ion line spectral source has some significance in this area in that it could assist in the reduction of source induced shot noise, consequently improving the detection limits for plasma source AAS.

There has recently been much interest in the application of sputtering sources in atomic spectrometry [P. Hannaford and A. Walsh, Spectrochim. Acta 43B, 1053 (1988)] [H.J. Kim and E.H. Piepmeier, Anal. Chem. 60, 2040 (1988)] [A.E. Bernhard, Spectroscopy, 2 No. 6, 24 (1987)]. Sputtering is the ejection of material from a surface caused by bombardment with an energetic beam of particles [B. Chapman, in Transactions of the Conference and School on the Elements, Techniques and applications of sputtering, 1 (1969)]. DC sputtering in a glow discharge source allows one to analyze solid samples by atomizing the analytes directly from the solid state. This approach offers some advantages. The time-consuming sample decomposition step can be omitted and analysis can be carried out without addition of reagents and without any separation and/or concentration steps so the risks of introducing contaminants and the loss of the element to be determined are considerably reduced. As a consequence an analysis can be carried out quite rapidly. It would appear that the sputtering rate should be a direct function of gas pressure, since the higher the pressure the more ions which would be available for sputtering. However, sputtering is usually carried out at pressures between $5 \times 10$ and 1 torr since glow discharges extinguish or switch over to arc discharges at higher pressures and the main sampling mechanism in arcs is thermal evaporation.

Although rf sputtering is not widely used as a sample introduction method in atomic spectroscopy, it has long been recognized as an important technique in sputter etching and chemical vapour deposition [B. Chapman, in Transactions of the Conference and School on the Elements, Techniques and applications of sputtering, 1 (1969)]. Rf sputtering at low pressures first suggested by Wehner in 1955 [G.K. Wehner, Advances in Electronics and Electron Phys., 7, 239 (1955)]and demonstrated in 1962 [G.S. Anderson, W.N. Mayer and G.K. Wehner, J. Appl. Phys., 33,2991 (1962)] has become a standard method for etching materials in the semiconductor industry. Atmospheric pressure rf sputtering was previously used by the inventors to supply Fe to the CCP discharge for the purpose of making temperature measurements. More recently, Stephens [R. Stephens, J. Anal. At. Spectrom. 3, 1137 (1988)] has described an rf discharge between two metal electrodes at atmospheric pressure, operating in helium at a power of 5-30 W. The sputtering effect of the discharge was deduced by observing atomic emission from the plasma and atomic absorpotion within the plasma. Stephens pointed out that this device offered a convenient means of observing either emission or absorpotion for those elements for which sputtering was not inhibited by the presence of a stable oxide layer.

SUMMARY OF THE INVENTION

A CCP which has application as a source for direct solid sample analysis is disclosed. In this description "source" describes devices primarily intended to be used as a means of vaporizing and exciting samples for analysis by emission methods.

We have discovered that the novel configuration of the CCP torch described previously by the inventors can be modified in order to carry out atmospheric pressure rf sputtering. The original CCP design has been modified to provide an excitation source for direct solid sample analysis. This modified CCP torch allows for a wide selection of plasma conditions, good control of sampling and excitation, and ease of interchange of samples for direct solids analysis applications.

A novel atmospheric pressure capacitively coupled radio frequency plasma discharge apparatus and method are disclosed. The system is suitable for atomic absorption and emission analysis of discrete sample volumes (1-50 $\mu$l) and direct solid samples. The plasma can be operated at very low Radio Frequency (RF) input powers (10-600 W) which allows for optimal conditions for atom resonance line absorption measurements. Sample introduction into the plasma can be done by an electrically heated tantalum strip vaporizer by atmospheric pressure rf sputtering. Analyte absorption takes place in the plasma discharge which is characterized by a long path length (10-50 cm) and low support gas flow rate (0.05 to 6 L/m) both of which provide for a relatively long residence time. The device exhibits linear calibration plots and provides sensitivities in the range of from 3.5-40 pg.

This invention is also directed to a novel RF plasma torch and sample introduction system which is designed for both atomic absorption spectrometry (AAS) and atomic emission spectrömetry (AES). This torch operates at atmospheric pressure at very low support gas flow rates and makes use of capacitive power coupling to form the plasma. Sample introduction into the plasma can be accomplished by using an electrically heated tantalum strip. In this way the sample vaporization and atomization steps are separated and can each be independently optimized. The discharge has a long path length tube geometry which is designed for atomic absorption measurements and this feature, in conjunction with the low support gas flow rates, maximizes analyte residence time.

The plasma is self-initiating and requires no ignition system. A capillary tube of an inside diameter of less than 1.5 mm prevents conduction of the plasma to the tantalum strip vaporizer. In the apparatus, the sample introduction means may be through the arc of cathode sputtering, electrical arcs or sparks, a graphite furnace, or hydride generation.

The invention is also directed to a method of generating and sustaining an atmospheric pressure plasma comprising utilizing a plasma containing volume having capacitively arranged electrodes enclosing at least a portion of the plasma containing volume, said electrodes being connected to a radio frequency generator and electrically insulated from the plasma.

In the method, the plasma may be operated at radio frequency input powers in the range of about 10 to 600 W. The plasma may be supported with a flowing support gas. The support gas may be selected from the group consisting of Ar, He, $N_2$, $H_2$, air and mixtures of these gases. The plasma may be supported with a support gas flowing at a rate of about 0.05 L/m to about 10 L/m.

With the method, atomic absorption or emission analysis may be conducted on a sample by vaporizing the sample and conveying the vaporized sample into the plasma with the support gas. The sample may be vaporized by sputtering and by rf sputtering. Atomic absorption or emission analysis may be conducted on a sample by introducing the sample into the plasma containing volume. A support gas and the sample may be introduced into the plasma containing volume at locations which may be proximate to each other. A support gas may be introduced into the plasma containing volume at one end thereof while the sample may be introduced into a mid-region of the plasma containing volume. Atmospheric pressure rf sputtering may be used to introduce vaporized atoms from the sample into the plasma containing volume. The sample may be introduced into the plasma containing volume with an electrically heated tantalum strip. The sample size may be between about 1 and about 50 μl.

The invention is also directed to an apparatus for generating and sustaining an atmospheric pressure capacitively generated plasma comprising: (a) hollow means for containing a plasma discharge; (b) two electrode means connected to a radio frequency power supply, electrically insulated from the plasma, and capacitively enclosing at least a portion of the hollow means.

In the apparatus, the hollow means may be a high melting point electrically insulating material. In the apparatus, the hollow means may be a square or rectangular cross-section shape quartz tube. The two electrodes may be elongated and are positioned in parallel on opposite sides of the quartz tube. The hollow means may be an elongated quartz tube which may have a generally square or rectangular cross-section and the two electrodes may be encased in quartz on opposite sides of and extend substantially along the length of the elongated quartz tube.

In the apparatus, a sample supporting means may penetrate into the plasma containing elongated quartz tube. A support gas inlet may introduce plasma support gas into the hollow quartz tube. A sample support means and the support gas inlet may be formed in the hollow quartz tube. The support gas may be introduced through an inlet at one end of the hollow quartz tube and the sample support means may be introduced into a mid-region of the hollow quartz tube. The sample support means and the support gas inlet may be positioned proximate to one another in a mid-region of the hollow quartz tube. The sample support means may be a tantalum strip connected to electrodes and a heat sink, and may be powered by a furnace power supply coupled to an rf filter. The sample support means may be separate from the hollow quartz tube and may be connected to the hollow quartz tube by a conduit. The sample support means may be a tantalum strip.

DRAWINGS

In the drawings, which illustrate specific embodiments of the invention, but which should not be regarded as limiting or restricting the spirit or scope of the invention in any way:

FIG. 1 depicts a side view of the capacitively coupled plasma discharge tube and sample vaporizer;

FIG. 1a depicts an end section view of the plasma discharge tube depicted in FIG. 1;

FIG. 3 depicts a plot of time resolved absorption and emission signals for 100 ng boron at 249.8 nm obtained using the capacitively coupled plasma;

FIGS. 11 depicts an enlarged view of the sampling section of the discharge tube depicted in FIG. 10.

FIG. 12 depicts a side view of a capacitively coupled plasma discharge tube with sample electrode in the plasma; and FIG. 12a depicts an end view of the discharge tube depicted in FIG. 12.

DETAILED DESCRIPTION OF A SPECIFIC EMBODIMENT OF THE INVENTION

Description of the Plasma Torch

An atmospheric pressure rf capacitively coupled plasma (CCP) has been demonstrated to be a powerful tool in both atomic absorption spectrometry (AAS), atomic emission spectrometry (AES) and gas chromatography (GC). The discharge design provides for very effective energy transfer from the power supply to the plasma by capacitive coupling. Therefore, the plasma can be generated at atmospheric pressure and in a flexible geometry. The plasma can be operated over a wide range of rf input powers (10–600 W) which allows for optimal conditions for atom resonance line absorption and emission measurements. The discharge can be formed in a long quartz tube 4 (20 cm in length) and runs at low support gas flow rates (0.05 L/min) both of which provide for a relatively long residence time of analyte atoms.

In one design sample introduction into the plasma is accomplished by using an electrically heated tantalum strip vaporizer. The analyte atoms that are vaporized from the tantalum strip are carried by the plasma gas into the plasma through a quartz capillary. In that case, the transportation efficiency is determined by the flow rate of the plasma gas. Greater gas flow rate gives higher the transportation efficiency, but shorter residence time of analyte atoms in the plasma.

Figure 2:
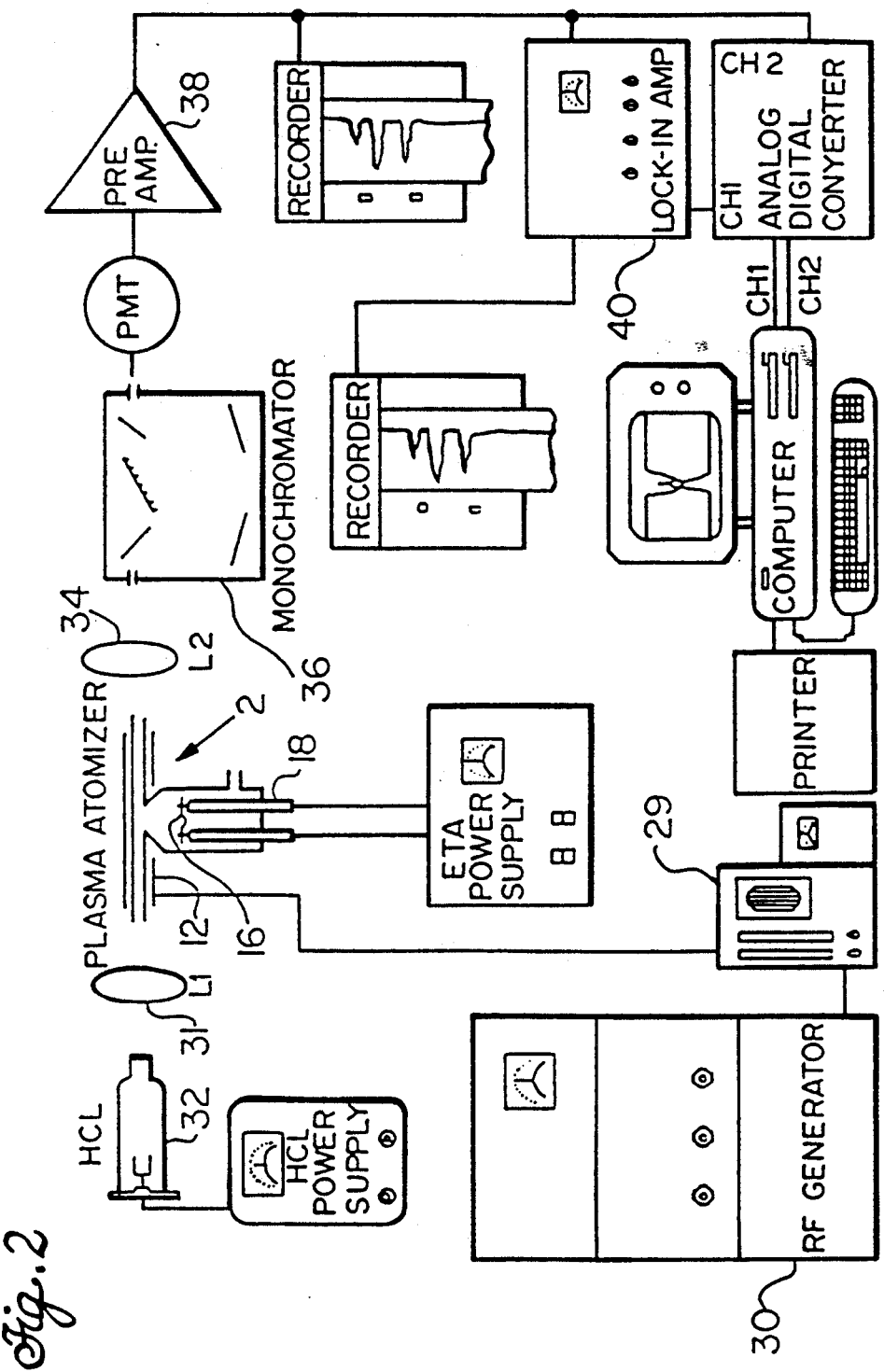
FIG. 2 depicts a schematic block diagram of the capacitively coupled plasma discharge tube with supporting hardware.

A schematic diagram of the device 2 is provided in FIG. 1. Functionally, the device 2 consists of two parts, the capacitively coupled plasma (CCP) discharge tube 4 and the tantalum strip electrothermal vaporization sample introduction system 6. The main body of both parts is constructed of quartz glass and the two parts are joined through a narrow neck 8 to form a T-shaped device. The plasma 9 is contained in a quartz tube 10, 20.0 cm in length and 0.4 cm inside diameter and 0.6 cm outside diameter. Power is coupled into the plasma using two stainless steel strips 12, 18.0 cm long and 0.5 cm wide, which are placed on either side of, and in contact with, the outside of this quartz tube 10 (see FIG. 1a for an end view). These stainless steel electrodes 12 are connected to the RF power supply (not shown in FIG. 1 but see FIG. 2). The plasma 9 has been operated using a fixed frequency 27.18 MHz RF supply and also with a 125-375 KHz variable frequency RF supply. It has been found that a stable plasma 9 can be sustained at RF powers ranging from 30–600 W. Plasma support gas is introduced using an inlet 14 on the side of the main body 6 of the quartz container. It has been determined that the discharge will operate at gas flow rates ranging from 0.2 to 6 L/m. The plasma 9 has been sustained using a variety of support gases including Ar, He, and mixtures of these gases with $N_2$, $H_2$, and air. Sample vaporization is accomplished using a tantalum strip 16 which is fastened to two copper rod conductors 18 which are connected to an electrothermal atomizer power supply (not shown but see FIG. 2). These electrodes 18 are surrounded by a water cooled jacket 20 with water inlet 22 and water outlet 24. Samples are placed on the tantalum strip vaporizer 16 through one of two ground glass tapered inlets 26 using a micropipette. Sample sizes vary from 1 to 50 $\mu l$.

The plasma torch that was developed previously by the inventors generated radio frequency plasma using capacitive coupling and a cylindrical plasma containing tube. It was found that when this torch works at a high rf power, the rf potential between the two electrodes is often high enough that there is a breakdown of the air medium outside the plasma torch. This causes detrimental arcing. Moreover the arcing might develop between the plasma column and the tantalum strip vaporizer, especially when easily ionized elements (EIE's) are vaporized from the tantalum strip into the plasma. Both types of arcings adversely change the plasma condition dramatically. To avoid these problems, the torch design depicted in FIGS. 1 and 1a has been developed. It has a 50 cm long quartz capillary with a diameter of 0.08 cm to connect the tantalum strip housing to the plasma tube. The longer the distance between the plasma column and the tantalum strip, the higher the rf breakdown potential that is required. High gas velocity in the quartz capillary prevents ions diffusing from the plasma to the tantalum strip housing. The arcing between the plasma column and tantalum strip is controlled effectively with these techniques. To avoid arcing outside the plasma torch, the cylindrical plasma column of the original plasma torch design has been replaced with a rectangular cross-section design with the electrodes positioned on each side and embedded in quartz.

DESCRIPTION OF EXPERIMENTAL FACILITIES (a) Equipment and Setuo. The experimental setup is schematically outlined in FIG. 2 and details of the equipment used are provided in Table I below. The CCP discharge was mounted inside a model PT-2500 torch box. Two systems were used. With System 1, power was coupled to the CCP 2 by inserting a secondary coil 29 into the normal ICP load coil. The leads from this secondary coil 29 were attached to the two stainless steel strip electrodes 12. With System 2, the stainless steel strip electrodes 12 were connected directly to the output of the RF generator 30. The CCP was run using both of the power supplies outlined in Table I. However, all of the results disclosed herein were collected using System 1. A plasma ignition system (test coil) was not required since it was found that the CCP automatically ignites upon application of approx. 100 W RF power.

A 25 cm focal length fused silica lens 31 was used to focus the hollow cathode lamp (HCL) 32 at the middle of the CCP tube (50 cm object distance) and a 10 cm focal length fused silica lens 34 was used to image the HCL and CCP onto the entrance slit of the monochromator 36 with object and image distances of 27 and 17 cm respectively. A stainless steel plate with a 0.4 cm hole (not shown) to cut down on the amount of unabsorbed HCL radiation and to reduce the plasma background reaching the entrance slit was placed at each end of the CCP discharge. Both absorption by, and emission from, analyte in the CCP discharge could be simultaneously measured, monitoring the output from both the preamplifier 38 and the lock-in-amplifier 40.

(b) Analytical Procedure. All absorption measurements were carried out using the following procedure. A 2-5 ul aqueous sample was placed on the tantalum strip 16 through the inlet port on the side of the quartz body. The plasma was off at this stage. The sample was dried and ashed. The plasma was then ignited at the end of the ash stage. The sample was then atomized. Data was collected through the atomize cycle. After each atomize cycle the atomizer was tested for a memory effect.

(c) Standard Solutions. All analytical standards were prepared using Fisher 1000 ppm atomic absorption standards. The solutions were diluted to volume using 1% $HNO_3$. A 1% $HNO_2$ solution was used as the reagent blank.

TABLE I

| Experimental Facilities and Operating Conditions | |
|---|---|
| Plasma Power Supply | System 1. Perkin-Elmer ICP 5500 System consisting of a Plasma-Therm (Kreeson, N.J.), HFP-2500F RF generator, AMN-2500E automatic matching network, APCS-3 automatic power control system and PT - 2500 torch box. System 2. ENI Power Systems Inc. (Rochester, N.Y.) Model HPG-2 RF Power Supply. Frequency: 125 KHz–375 KHz., Output Power: 0–200 W. |
| Sample Vaporization | Tantalum strip 1.5 cm by 0.5 cm with a depression at the center. Power: Varian Model CRA-61. Normal operating cycle: Dry - 105 C for 60 s, Ash - 300–600 C for 15 s, Atomize - 2000–3700 C for 2 s. |
| Spectrometer | Schoeffel-McPherson (Acton, MA) Model 270, 0.35 m Czerny-Turner mount scanning monochromator with 600 rulings/mm holographic grating. Reciprocal linear dispersion of 40 °-A/mm in the first order. |
| Slits | Entrance and exit slits set to 50 um for Mn determination, and 21 um for intensity ratio measurement. |
| Hollow Cathode Lamps | Hollow cathode lamps (HCL) were powered using a home-built, electronically modulated power supply. Modulation frequency - 250 Hz and a duty cycle of 50%. Normal operating currents were used for the lamps. |
| Detector Electronics | The photocurrent from a Hammatsu R955 photomultiplier tube was amplified by a home-built preamplifier and fed to a Princeton Applied Research Model 121 Lock-In-Amplifier. The photomultiplier tube was powered using a McPherson Model EU-42A PMT powe supply. |
| Data Acquisition | Digital data acquisition was carried out using a Tulsa Computers (Owasso, OK) Telex Model 1280 IBM- At compatible computer equipped with an RC Electronics (Santa Barbara, CA) Model ISC-16 analog-digital converter running the RC Computerscope software package. Analog data was acquired using a |

TABLE I-continued

Experimental Facilities and Operating Conditions

Servocorder 210 chart recorder.

Results

We have noted that Ar-CCP can be generated as soon as the RF power is applied to the discharge tube. The plasma is light blue in color and fills the discharge tube 4 but does not enter the inlet 26 nor is any arcing observed between the plasma and the tantalum strip 16. The plasma appears stable without any observable flicker or modulation and fills the discharge tube uniformly. At support gas flow rates less than 4 L/m the plasma is contained inside the quartz discharge tube 4, but at support gas flow rates exceeding 4 L/m a small plasma jet can be seen emanating from each end of the discharge tube. When a sample containing a relatively high concentration of Li is vaporized, a red band of Li emission can be observed to move from the junction of the T down the length of each branch of the discharge tube 10. The device 2 has also been found to operate with no difficulty on pure He and on Ar-$H_2$, Ar-$N_2$, Ar-air, He-$H_2$, He-$N_2$, and He-air mixtures. The addition of $H_2$, $N_2$, and air to the argon support gas allows for the adjustment of excitation conditions in the plasma and permits the discharge to provide either an inert, oxidizing, or reducing environment. It is anticipated that this feature will prove to be very useful for the future application of the device to different sample types. For example, a reducing environment can be created by using an Ar-$H_2$ mixture. This should help to control the formation of refractory oxides in the discharge.

Typical time resolved absorption and emission signals acquired from the CCP are provided in FIG. 3. To record these signals, 100 ng of B was introduced onto the tantalum strip 16, vaporized into the Ar plasma discharge and emission and absorption for the BI 249.8 nm line measured. The power used was 400 W and the support gas flow rate was 1.2 L/m. The origin on the time axis, which is marked in units of seconds, corresponds to the beginning of the atomization cycle. The vertical (signal) axis is in arbitrary units. The apparent noise on the emission signal is from the modulated hollow cathode lamp. The signals start to appear after about 0.9 s and persist for about 0.6 s following first appearance. The underlying background is relatively flat for both absorption and emission and is not appreciably affected by the vaporization step.

Figure 4:
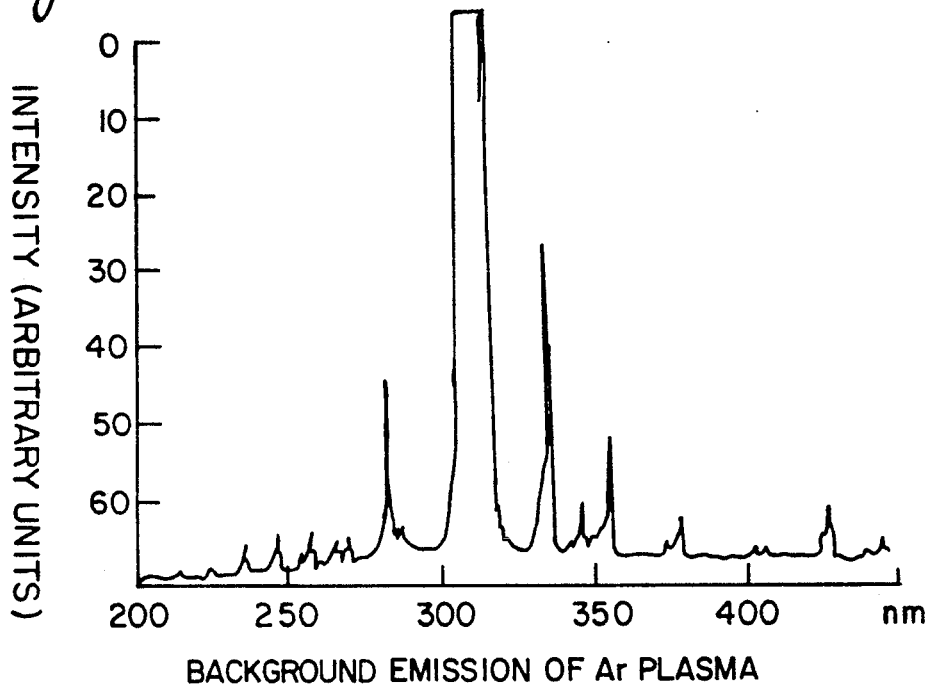
FIG. 4 depicts a background emission spectrum of the capacitively coupled plasma using argon as a support gas.
Figure 5:
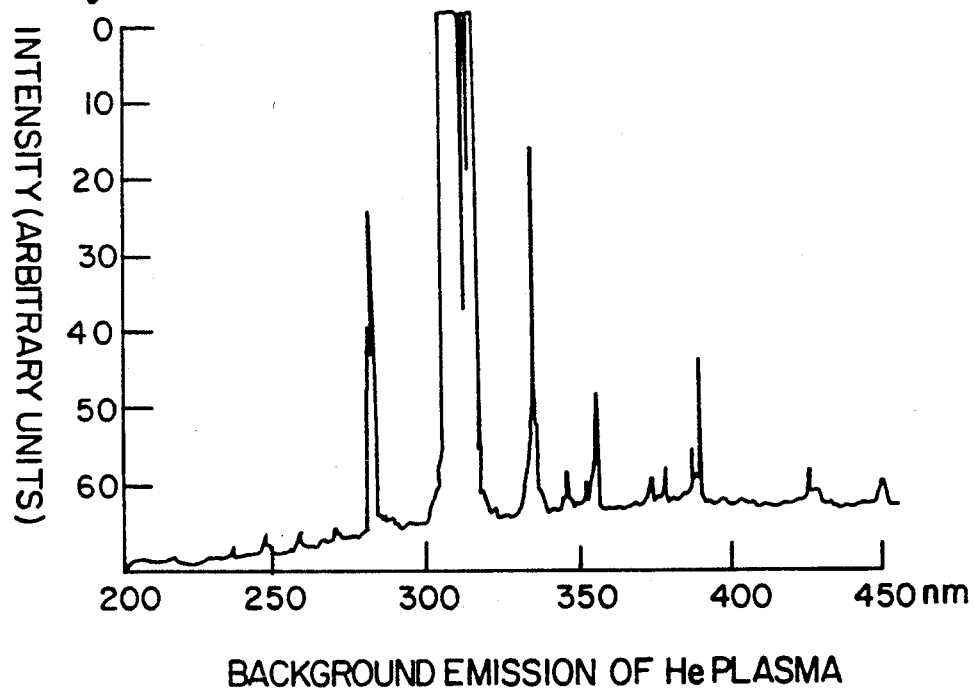
FIG. 5 depicts a background emission spectrum of the capacitively coupled plasma using helium as a support gas.
Figure 6:
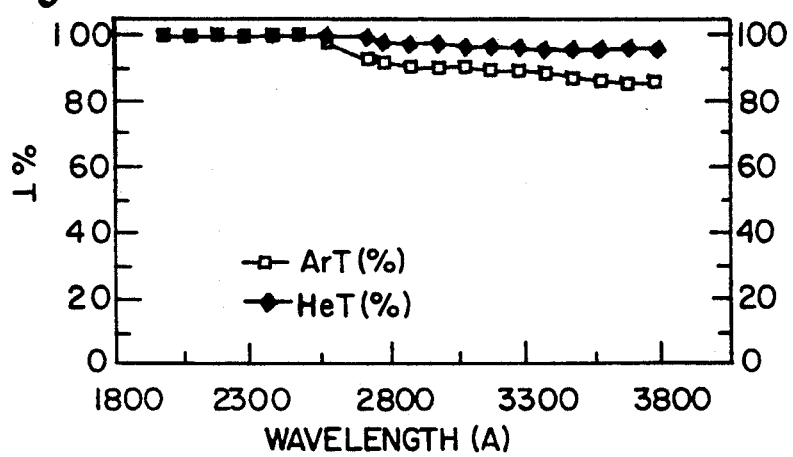
FIG. 6 depicts the transmittance of argon—capacitively coupled plasma and helium—capacitively coupled plasma over a specified wavelength range.

Background emission from the Ar-CCP and He-CCP recorded over the wavelength range 200–450 nm at an RF power of 200 W are provided in FIGS. 4 and 5 respectively. In both of these plasmas, the main spectral features are OH emission in the 280–285 nm and 302–317 nm regions and NO emission in the 215–272 nm region. The transmittance of the Ar-CCP and He-CCP over the wavelength range 200–380 nm at an RF power of 200 W is recorded in FIG. 6. This was recorded using a $D_2$ lamp and measuring the broadband % T at 10 nm intervals. The transmittance decreases with an increase in wave-length for both plasmas. For the HeCCP the transmittance is greater than 95% and for the Ar-CCP it is greater than 85% over this wavelength range.

An iron atom excitation temperature was measured using a method previously described by the inventors in the literature (M.W. Blades and B.L. Caughlin, Spectrochim. Acta, 1985, 40B, 579). A section of iron wire was introduced into the plasma at the junction of the "T" to provide a source of iron atoms. The collection optics were set up to image the center of the discharge onto the entrance slit of the monochromator. Emission from a set of seven FeI lines in the region 370–385 nm covering an energy range from 27000 to 35000 cm$^{-1}$ were used for this measurement. The lines used were the same as those which were outlined in the M.W. Blades et al. reference above. A Schoeffel-McPherson (Acton, MA) Model 2061 1-meter monochromator equipped with a linear photodiode array was used to carry out the measurement. The complete system has been described elsewhere (see Z.H. Walker and M.W. Blades, Spectrochim. Acta, 1986, 41B, 761). The temperature was measured at an RF input power of 400 W and a support gas flow rate of 0.6 L/m. A linear regression slope temperature indicated a temperature of 3960 +/−300° K at this power. One of the co-inventors, with another, has previously measured FeI excitation temperatures for a low-flow, low-power ICP system and found a temperature of 4000° K at an RF power of 400 W (see L.L. Burton and M.W. Blades, Appl. Spectrosc., 1986, 40, 265). Also, for the ICP, the temperature was found to have a roughly linear relationship with power. An extrapolation to 100 W suggests that the temperature at this power should be on the order of 3000–3500° K, in the same range as that found in $N_2O$ acetylene flames.

Figure 7:
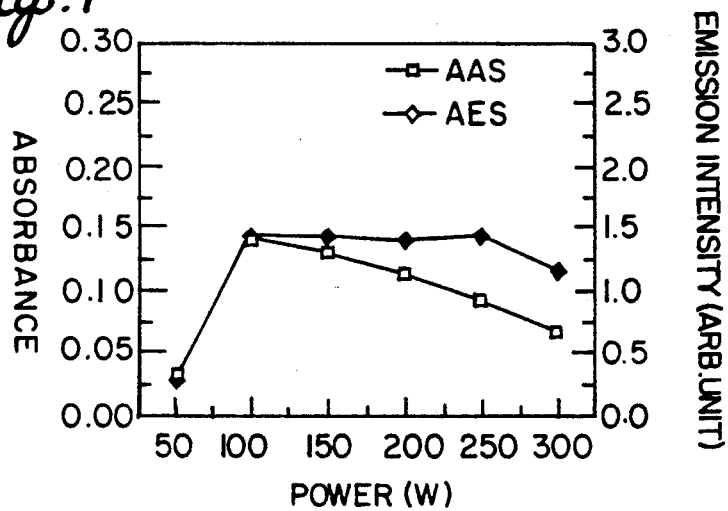
FIG. 7 depicts a graphical depiction of absorbance, power and emission intensity for atomic absorption spectroscopy and atomic emission spectroscopy.

The effect of changes in RF input power on absorption and emission signals of the AgI 328.1 nm line was studied at a support gas flow rate of 1.0 L/m. The results over the power range 50–300 W are provided in FIG. 7. The optimal RF power for this line was found to be between 100 and 200 W. At a power of 50 W the absorption and emission signals drops to 0 and at powers higher than 200 W the absorbance decreases steadily. At the low end of the power scale, it is suspected that the formation of undissociated gas phase molecules reduces the sensitivity, and at the high end, the formation of Ag ions reduces the sensitivity.

Figure 8:
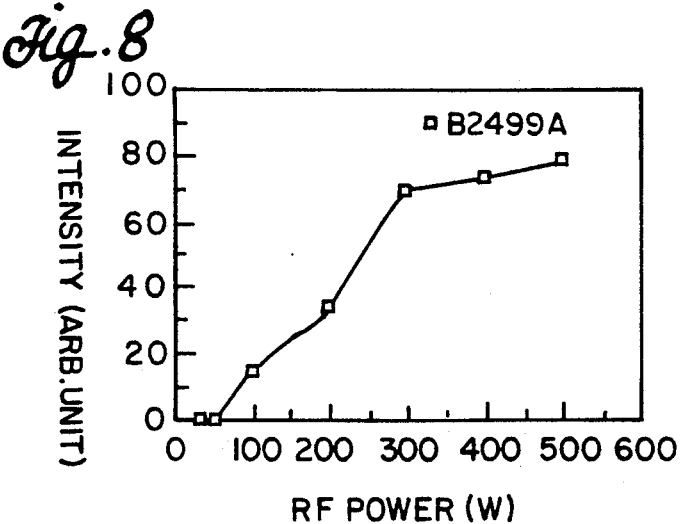
FIG. 8 depicts the effect of rf power on emission intensity of boron.

The effect of rf power from 50 to 500 W on the emission (intensity) signal for BI 249.8 nm line at a gas flow rate of 1.25 L/m is depicted in FIG. 8. Boron emission signals generally increase with an increase in rf power input.

Figure 9:
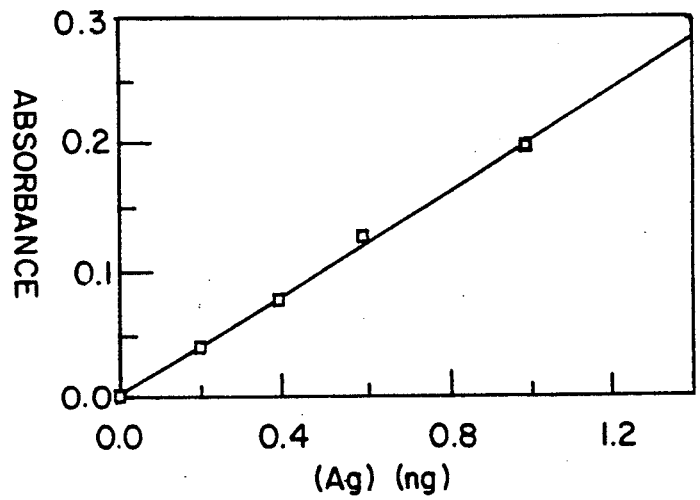
FIG. 9 depicts an absorbance calibration plot for AgI 328.1 nm.

To check on analytical performance, a support gas flow rate of 0.6 L/m and an RF input power of 150 W were chosen as the working conditions. An absorbance calibration plot from 0 to 1 ng for the AgI 328.1 nm line is provided in FIG. 9. The CCP device exhibits good linearity over the concentration range 0–10 ng total analyte. A listing of 0.0044 absorbance unit sensitivities and detection limits for atomic emissions is provided in Table II below for Ag, Cd, Cu, Li, Sb and B for the plasma system described in this disclosure and for conventional graphite furnace AAS (see C.W. Fuller, "Electrothermal Atomization for Atomic Absorption Spectrometry", Analytical Sciences Monograph, the Chemical Society, London (1977)). It can be seen that the sensitivities for the CCP device are in the range of from 3.5 to 2000 pg and the detection limits for CCP-AES are in the range of from 0.7 to 400 pg depending on the element involved and are comparable to or better than those obtained with a graphite furnace.

The atmospheric pressure capacitively coupled plasma described herein is a new atom reservoir and source for carrying out elemental analysis using atomic absorption and emission spectroscopy. It has been designed for the analysis of small sample volumes of a size typically analyzed using furnace atomic absorption. However, it is also possible to introduce dried aerosol or hydrides through the support gas inlet when continuous sample introduction is desired. The plasma discharge tube and sample introduction device allows for the separate control of the vaporization and atomization environments. This new spectrochemical source has a long absorption path length which provides extended analyte residence times when compared with a graphite furnace. As demonstrated, the plasma can be operated at very low support gas flow rates which further enhances the analyte residence time. Also, since the analyte is embedded in a plasma environment, vapour phase condensation is not a problem. Preliminary results of temperature measurement yield a value of around 4000° K. At this temperature, potential chemical interferences should be minimized. The ability to operate on a variety of pure support gases and gas mixtures permits the atomization environment to be made inert, reducing, or oxidizing as the analysis situation demands.

To increase the transportation efficiency and residence time, the tantalum strip evaporizer can be inserted into the plasma as illustrated in the embodiments depicted in FIGS. 10, 10a, 11, 12 and 12a. These devices combine advantages of both the electrothermal atomizers and the CCP. In this way, we have achieved better detection limits than by inductively coupled plasma atomic emission spectrometry (ICP-AES), and less interference effects than by graphite furnace atomic absorption spectrometry (GF-AAS). Additional atomization by atmospheric pressure rf sputtering has been used in the CCP. High yield provided by atmospheric rf sputtering gives a better atomization device than other electrothermal atomizers.

Figure 10:
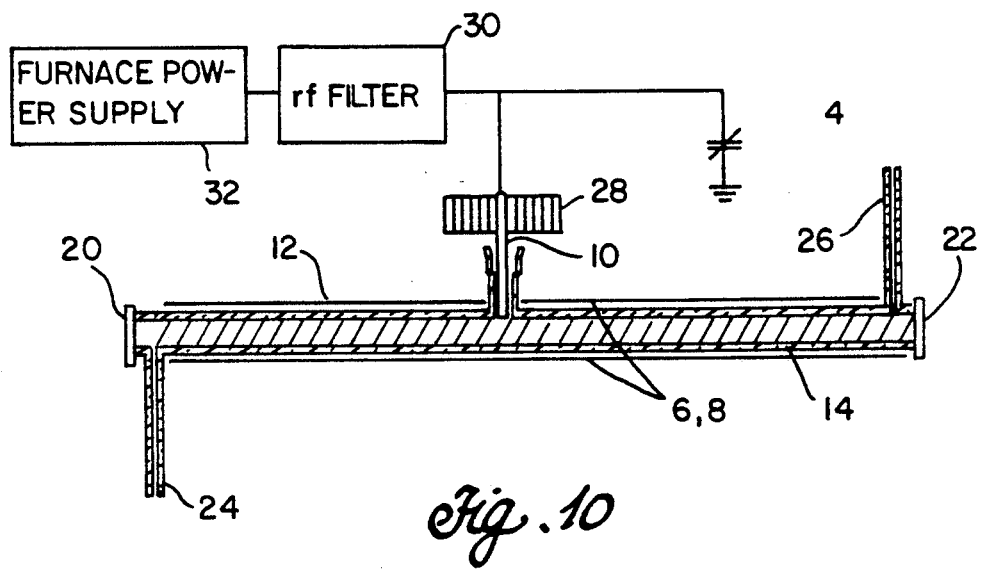
FIG. 10 depicts a side view of a capacitively coupled plasma discharge tube with heat sink.
Figure 10A:
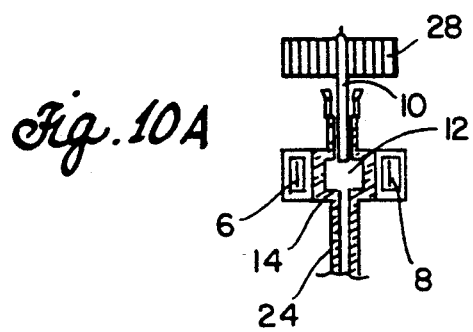
FIG. 10a depicts an end view of the discharge tube depicted in FIG. 10.

FIGS. 10 and 10a depict side and end section views of a configuration of the capacitively coupled plasma and sampling system where an end of the sample electrode 40 is in the plasma. In the embodiment depicted in FIGS. 10 and 10a, a quartz torch 4 cooperates with electrodes 6 and 8 to generate a plasma 12 in the square cross-section tube 14. A sample electrode 10 penetrates into the plasma 12 in the interior of the tube 14. This design is especially useful for direct solid sample analysis by atmospheric rf sputtering and to increase transportation efficiency and residence time. A pair of quartz windows 20 and 22 are located at each end of the tube 14 to contain the plasma. Also a pair of argon inlets and outlets 24 and 26 are located at each end of the tube 14. A heat sink 28 is mounted at the top of the sample electrode 10 to absorb heat from the electrode. The electrode 10 is connected to an rf filter 30 and a furnace power supply 32.

FIG. 11 depicts an enlarged side view of the sample electrode and heat sink construction. The electrode 10 is constructed of a pair of electrodes 40 and 42 connected to a tantalum strip 44 by pins 46. A macor centre 48 is disposed between the electrodes 40 and 42. The heat sink 28 is mounted at the top portion of the electrodes 40 and 42.

A side view of an alternative embodiment of a direct plasma sampling device 2 is depicted in FIG. 12. Functionally, the device 2 consists of three basic parts, the capacitively coupled plasma (CCP) quartz torch 4, a pair of electrodes 6 and 8 connected to an rf power supply, and a tantalum strip electrothermal vaporization electrode 10 with its lower end extending into the tube 14. The body of the torch 4 is constructed of quartz glass and is in the form of a T-shape. The plasma 12 is contained in a square cross-section quartz tube 14 which is about 20.0 cm in length. Power is coupled into the plasma 12 using two stainless steel electrodes 6 and 8 which are sealed in quartz on either side of, and in contact with, the outside of the quartz tube 14 (see FIG. 12a for an end view). These stainless steel electrodes 6 and 8 are connected to an RF power supply (not shown in FIG. 12 but see FIG. 2). The plasma 12 has been operated using a fixed frequency 27.18 MHz RF supply and also with a 125-375 KHz variable frequency RF supply. It has been found that a stable plasma 12 can be sustained at RF powers ranging from 30-600 W. Plasma support gas is introduced using an inlet 16 on the underside of the main body 14 of the quartz torch 4. It has been discovered that the plasma discharge will operate at gas flow rates ranging from 0.2 to 6 L/m. The plasma 12 has been sustained using a variety of support gases including Ar, He, and mixtures of these gases with $N_2$, $H_2$, and air. Sample vaporization is accomplished using a tantalum strip 10 which is fastened to copper rod conductors 18 which are connected to an electrothermal atomizer power supply (not shown). When the sample electrode 10 is inserted into the plasma through the central sampling port 11, Teflon tape is wrapped on the sample rod 10 to provide a gas seal. A 25 pF air-medium variable capacitor is placed in series with the sample electrode 10 and is connected to the rf power supply ground. Since the plasma potential is higher than ground, the electrode provides a path for rf current. The main advantage of this design is that the rf current in the sample rod 10 can be controlled using the capacitor which in turn controls the sample rod temperature and the sampling rate. This prevents the sample rod from melting at high input powers. Another advantage is that the device can be used with both atomic emission and absorption measurement systems.

The constructions depicted in FIGS. 1, 1a, 10, 10a, 11, 12 and 12a have the following advantages over prior designs (a) They inhibit or prevent arcing between the two electrodes outside the plasma torch. The CCP torch can therefore run at high rf input power.

(b) The plasma is more uniform than in a prior CCP design.

(c) The device is more easy to construct the prior CCP torch.

TABLE II

| | Sensitivies and Wavelengths for Ag, Cd, Cu, Li, B and Sb. | | | |
|---|---|---|---|---|
| | | Sensitivity (pg) | | Detection Limit (pg) |
| Element | Wavelength (nm) | CCP-AAS | GF-AAS[13] | CCP-AES |
| Ag | 328.1 | 10 | 5 | 0.7 |
| Cd | 228.8 | 3.5 | 1 | 0.7 |
| Cu | 324.8 | 40 | 30 | |
| Li | 670.8 | 23 | 10 | 2 |
| Sb | 217.6 | 24 | 20 | 80 |

TABLE II-continued
Sensitivies and Wavelengths for Ag, Cd, Cu, Li, B and Sb.

| Element | Wavelength (nm) | Sensitivity (pg) | | Detection Limit (pg) |
|---|---|---|---|---|
| | | CCP-AAS | GF-AAS[13] | CCP-AES |
| B | 249.8 | 2000 | 1000 | 400 |

The CCP torch configurations described herein provide for very effective energy transfer by capacitive coupling allowing a plasma to be generated at atmospheric pressure. They offer a uniform and stable plasma medium which has potential applications in many areas. The novel CCP has been used as a source for direct conducting solids analysis using atmospheric pressure rf sputtering. Rf sputtering at atmospheric pressure is characterized by a relatively high density of bombarding particles resulting in a high sputtering yield. This leads to high analyte emission intensities from the CCP source.

At this point, the atmospheric pressure rf sputtering CCP source shows potential for the analysis of conductive solids directly and non-conductive solids by mixing with graphite or copper powders and then pressing them into pins. It is also possible to analyze micro-liter volumes of liquid solutions by deposition on the surface of graphite or metal rods. Analysis of flat conducting sheets can be accomplished by modifying the CCP torch to accept flat samples.

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A method of conducting atomic absorption or emission analysis on a sample by vaporizing the sample in a manner so that it is introduced into a gas-supported atmospheric pressure plasma comprising utilizing an elongated quart chamber of rectangular or square cross section as a plasma container, the chamber having on opposite elongated sides thereof capacitively arranged elongated planar electrodes encased in quartz and enclosing at least a portion of the length of the plasma containing chamber, said electrodes being connected to a radio frequency generator and electrically insulated from the plasma, and conducting atomic absorption or emission analysis on the vaporized sample in the plasma.

2. A method as defined in claim 1 wherein the plasma is operated at radio frequency input powers in the range of about 10 to 600 W.

3. A method as defined in claim 2 wherein the plasma is supported with a flowing support gas.

4. A method as defined in claim 3 wherein the support gas is selected from the group consisting of Ar, He, $N_2$, $H_2$, air and mixtures of these gases.

5. A method as defined in claim 4 wherein the plasma is supported with the support gas flowing at a rate of about 0.05 L/m to about 10 L/m.

6. A method as defined in claim 3 wherein atomic absorption or emission analysis is conducted on the sample by vaporizing the sample in the chamber and conveying the vaporized sample into the plasma with the support gas.

7. A method as defined in claim 6 wherein the sample is vaporized by sputtering.

8. A method as defined in claim 6 wherein the sample is vaporized by rf sputtering.

9. A method as defined in claim 1 wherein a support gas and the sample are introduced into the plasma containing chamber at locations which are proximate to each other.

10. A method as defined in claim 1 wherein a support gas is introduced into the plasma containing chamber at one end thereof while the sample is introduced into a mid-region of the plasma containing chamber.

11. A method as defined in claim 1 wherein atmospheric pressure rf sputtering is used to introduce vaporized atoms from the sample into the plasma containing chamber.

12. A method as defined in claim 1 wherein the sample is introduced into the plasma containing chamber with an electrically heated tantalum strip.

13. A method as defined in claim 1 wherein the sample size is between about 1 and about 50 µl.

14. An apparatus for conducting atomic absorption or emission analysis on a sample by vaporizing the sample in an atmospheric pressure capacitively generated plasma comprising:
(a) elongated hollow means constructed of an electrically insulating material having a generally rectangular or square cross section for containing a plasma discharge;
(b) two planar electrodes connected to a radio frequency power supply, the planar electrodes being encased in an electrically insulating material and being electrically insulated from the plasma, and capacitively enclosing at least a portion of each elongated side of the hollow means by being positioned on opposite elongated sides of the rectangular or square cross section hollow means;
(c) means for supporting and vaporizing the sample to be analyzed;
(d) inlet means into the elongated hollow means for enabling a plasma support gas to be conveyed through the elongated hollow means;
(e) connection means for enabling the vaporized sample to be introduced into the elongated hollow means; and
(f) analysis means for conducting atomic absorption or emission analysis on the vaporized sample.

15. An apparatus as defined in claim 14 wherein the hollow means is a high melting point electrically insulating material.

16. An apparatus as defined in claim 14 wherein the hollow means is a square or rectangular cross-section shape quartz tube.

17. An apparatus as defined in claim 16 wherein the two electrodes are elongated and are positioned in parallel on opposite sides of the quartz tube.

18. An apparatus as defined in claim 14 wherein the hollow means is an elongated quartz tube which has a generally square or rectangular cross-section and the two electrodes are encased in quartz on opposite sides of and extend substantially along the length of the elongated quartz tube.

19. An apparatus as defined in claim 18 wherein the sample supporting means penetrates into the plasma containing elongated quartz tube.

20. An apparatus as defined in claim 19 wherein said inlet means introduces said plasma support gas into the hollow quartz tube.

21. An apparatus as defined in claim 20 wherein the sample support means and the inlet means extend into the hollow quartz tube.

22. An apparatus as defined in claim 21 wherein the support gas is introduced through the inlet means at one end of the hollow quartz tube and the sample support means is introduced into a mid-region of the hollow quartz tube.

23. An apparatus as defined in claim 21 wherein the sample support means and the gas inlet means are positioned proximate to one another in a mid-region of the hollow quartz tube.

24. An apparatus as defined in claim 21 wherein the sample support means is a tantalum strip connected to the electrodes and a heat sink, and is powered by a furnace power supply coupled to an rf filter.

25. An apparatus as defined in claim 18 wherein the sample support means is separate from the hollow quartz tube and is connected to the hollow quartz tube by a conduit.

26. An apparatus as defined in claim 25 wherein the sample support means is a tantalum strip.

27. An apparatus for enabling atomic absorption or emission analysis to be conducted on a vaporized sample in an atmospheric pressure capacitively generated plasma which comprises:

(a) an elongated open-ended hollow quartz tube having planar sides and a generally rectangular or square cross section adapted for containing the plasma;

(b) a pair of stainless steel elongated planar electrodes connected to a radio frequency power supply, the electrodes being encased in quartz and being positioned in alignment with and on opposed elongated sides of the square or rectangular cross-sectional shaped tube;

(c) a tantalum sample support means for enabling a sample to be vaporized by applying electrical current from an electrothermal atomizer power supply to the tantalum sample support means;

(d) means for extracting heat from the tantalum sample support;

(e) means for enabling the vaporized sample to enter and commingle with the plasma contained in the quartz tube at a mid-point in the plasma;

(f) said quartz tube having an opening proximate to means (e) for enabling plasma support gas to be conveyed to and support the plasma;

(g) a furnace power supply connected through a rf filter to the tantalum sample support means; and (h) means for conducting atomic absorption or emission analysis on the vaporized sample in the plasma.

28. An apparatus as defined in claim 27 further comprising means to close the quartz tube at each end with transparent quartz windows and wherein an opening is located proximate to each end of the quartz tube for enabling plasma support gas to be introduced through one opening and withdrawn through the other opening.

* * * * *